United States Patent
Ganesh et al.

(10) Patent No.: US 10,067,203 B2
(45) Date of Patent: Sep. 4, 2018

(54) ENERGY STORAGE SOLUTION FOR AN MRI SYSTEM

(71) Applicant: GENERAL ELECTRIC COMPANY, Schenectady, NY (US)

(72) Inventors: Jayanti Ganesh, Bangalore (IN); Juan Antonio Sabate, Niskayuna, NY (US); Rajendra Naik, Bangalore (IN); Margaret Ann Wiza, Brookfield, WI (US); Viswanathan Kanakasabai, Bangalore (IN); Michael Thomas Rose, Milwaukee, WI (US)

(73) Assignee: GENERAL ELECTRIC COMPANY, Schenectady, NY (US)

(*) Notice: Subject to any disclaimer, the term of this patent is extended or adjusted under 35 U.S.C. 154(b) by 174 days.

(21) Appl. No.: 14/879,775

(22) Filed: Oct. 9, 2015

(65) Prior Publication Data
US 2017/0102441 A1 Apr. 13, 2017

(51) Int. Cl.
| | |
|---|---|
| H02J 3/00 | (2006.01) |
| G01R 33/36 | (2006.01) |
| A61B 5/055 | (2006.01) |
| G01R 33/385 | (2006.01) |
| G01R 33/389 | (2006.01) |
| H02J 9/06 | (2006.01) |
| H02M 7/04 | (2006.01) |
| G01R 33/28 | (2006.01) |

(52) U.S. Cl.
CPC ............ *G01R 33/36* (2013.01); *A61B 5/055* (2013.01); *G01R 33/28* (2013.01); *G01R 33/3614* (2013.01); *G01R 33/389* (2013.01); *G01R 33/3852* (2013.01); *H02J 9/061* (2013.01); *H02M 7/04* (2013.01)

(58) Field of Classification Search
USPC ..................................... 307/11, 18; 324/322
See application file for complete search history.

(56) References Cited

U.S. PATENT DOCUMENTS 4,027,171 A 5/1977 Browder et al.
5,270,657 A * 12/1993 Wirth ................. G01R 33/3852
324/318

(Continued)

FOREIGN PATENT DOCUMENTS

JP 5367293 B2 12/2013
KR 20140053282 A 5/2014

OTHER PUBLICATIONS

Ristic, Milailo, et al.; "Supercapacitor Energy Storage for Magnetic Resonance Imaging Systems"; Industrial Electronics, IEEE Transactions, vol. 61, Issue 8, pp. 4255-4264; Aug. 2014.

(Continued)

*Primary Examiner* — Adam Houston
(74) *Attorney, Agent, or Firm* — GE Global Patent Operation; Pabitra Chakrabarti

(57) ABSTRACT

The present disclosure relates possible implementations for utilizing energy storage elements in conjunction with a MRI system. Similarly, various associated control mechanisms are discussed. In certain embodiments, one or both of peak power shaving or energy backup may be facilitated by use of the energy storage elements. Certain such implementations may facilitate the use of higher-power MRI systems with an existing electrical infrastructure.

19 Claims, 12 Drawing Sheets

(56) References Cited

U.S. PATENT DOCUMENTS

| | | | | |
|---|---|---|---|---|
| 5,570,022 A * | 10/1996 | Ehnholm | G01R 33/381 | 324/318 |
| 5,659,465 A | 8/1997 | Flack et al. | | |
| 5,701,076 A * | 12/1997 | Schmitt | G01R 33/3852 | 324/322 |
| 5,721,490 A * | 2/1998 | Takano | G01R 33/3852 | 324/322 |
| 5,999,001 A * | 12/1999 | Kuhara | G01R 33/3852 | 324/314 |
| 6,025,720 A * | 2/2000 | Lenz | G01R 33/3852 | 324/318 |
| 6,154,031 A * | 11/2000 | Hughes | G01R 33/3852 | 324/318 |
| 6,323,649 B1 * | 11/2001 | Pace | G01R 33/3852 | 324/318 |
| 6,900,638 B1 * | 5/2005 | Yair | G01R 33/3852 | 324/309 |
| 7,099,130 B2 | 8/2006 | Angle et al. | | |
| 8,174,225 B2 | 5/2012 | Mazumdar et al. | | |
| 8,278,927 B2 * | 10/2012 | Venkatesa | H02M 7/487 | 324/309 |
| 8,446,037 B2 | 5/2013 | Williams | | |
| 8,657,787 B2 | 2/2014 | Neer | | |
| 8,692,412 B2 * | 4/2014 | Fiorello | H01Q 1/02 | 307/104 |
| 9,116,676 B2 | 8/2015 | Izquierdo et al. | | |
| 2009/0309598 A1 | 12/2009 | Zhu et al. | | |
| 2011/0139550 A1 | 6/2011 | Veronesi | | |
| 2011/0160564 A1 * | 6/2011 | Alford | G01R 33/445 | 600/410 |
| 2011/0187369 A1 * | 8/2011 | Rivas Davila | G01R 33/3852 | 324/318 |
| 2011/0279117 A1 * | 11/2011 | Alford | A61K 49/103 | 324/307 |
| 2011/0291655 A1 * | 12/2011 | Hamamura | G01R 33/3642 | 324/318 |
| 2013/0033118 A1 | 2/2013 | Karalis et al. | | |
| 2013/0099581 A1 | 4/2013 | Zhou et al. | | |
| 2013/0113280 A1 | 5/2013 | Yang et al. | | |
| 2013/0307540 A1 * | 11/2013 | Taracila | G01R 33/34007 | 324/318 |
| 2014/0009151 A1 | 1/2014 | Van Helvoort | | |
| 2014/0253120 A1 | 9/2014 | Ugurbil et al. | | |
| 2014/0300362 A1 | 10/2014 | Kawajiri et al. | | |
| 2014/0354234 A1 | 12/2014 | Sudan et al. | | |
| 2015/0005616 A1 * | 1/2015 | Saha | G01R 33/422 | 600/411 |
| 2015/0054509 A1 * | 2/2015 | Smits | G01R 33/3852 | 324/322 |
| 2015/0069850 A1 * | 3/2015 | Vollaire | H04W 52/0229 | 307/104 |
| 2015/0171768 A1 | 6/2015 | Perreault | | |
| 2015/0377994 A1 * | 12/2015 | Gui | G01R 33/56536 | 324/309 |
| 2015/0377996 A1 * | 12/2015 | Carl | G01R 33/4816 | 324/309 |
| 2016/0007853 A1 * | 1/2016 | Slavin | A61B 5/0044 | 600/413 |
| 2016/0187434 A1 * | 6/2016 | Boskamp | G01R 33/34076 | 324/309 |
| 2016/0187447 A1 * | 6/2016 | Hwang | G01R 33/4828 | 324/309 |
| 2016/0299207 A1 * | 10/2016 | Guidon | G01R 33/56341 | |
| 2017/0003370 A1 * | 1/2017 | Chen | G06T 7/0012 | |
| 2017/0038443 A1 * | 2/2017 | Ebel | G01R 33/36 | |
| 2017/0102441 A1 * | 4/2017 | Ganesh | A61B 5/055 | |
| 2017/0176627 A1 * | 6/2017 | Venkataramanan | G01V 3/32 | |
| 2017/0176628 A1 * | 6/2017 | Paulsen | G01V 3/32 | |
| 2017/0237293 A1 * | 8/2017 | Faraone | H02J 50/90 | 713/300 |

OTHER PUBLICATIONS

Grbovic et al., "The Ultracapacitor-Based Regenerative Controlled Electric Drives With Power-Smoothing Capability", Industrial Electronics, IEEE Transactions on, vol. No. 59, issue No. 12, pp. 4511-4522, Jan. 2, 2012.

PCT Search Report and Written Opinion issued in connection with corresponding PCT Application No. PCT/US2016/055650 dated Jan. 10. 2017.

* cited by examiner

ENERGY STORAGE SOLUTION FOR AN MRI SYSTEM

BACKGROUND

The subject matter disclosed herein relates to medical imaging systems and, in particular, to addressing the power requirements of a magnetic resonance imaging system.

Non-invasive imaging technologies allow images of the internal structures or features of a patient to be obtained without performing an invasive procedure on the patient. In particular, such non-invasive imaging technologies rely on various physical principles, such as the differential transmission of X-rays through the imaged volume or the gyromagnetic properties of materials within the imaged volume, to acquire data and to construct images or otherwise represent the observed internal features of the patient.

For example, in general, magnetic resonance imaging (MRI) examinations are based on the interactions among a primary magnetic field, a radiofrequency (RF) magnetic field, and time varying magnetic gradient fields with a gyromagnetic material having nuclear spins within a subject of interest, such as a patient. Certain gyromagnetic materials, such as hydrogen nuclei in water molecules, have characteristic behaviors in response to external magnetic fields. The precession of spins of these nuclei can be influenced by manipulation of the fields to produce RF signals that can be detected, processed, and used to reconstruct a useful image.

The magnetic fields used to generate images in MRI systems include a highly uniform, static magnetic field that is produced by a primary magnet. A series of gradient fields are produced by a set of gradient coils located around the imaging volume in which the subject is placed. The gradient fields encode positions of individual plane or volume elements (pixels or voxels) in two or three dimensions. An RF coil is employed to produce an RF magnetic field. This RF magnetic field perturbs the spins of some of the gyromagnetic nuclei from their equilibrium directions, causing the spins to precess around the axis of their equilibrium magnetization. During this precession, RF fields are emitted by the spinning, precessing nuclei and are detected by either the same transmitting RF coil, or by one or more separate coils. These signals are amplified, filtered, and digitized. The digitized signals are then processed using one or more algorithms to reconstruct a useful image.

MRI images provide a variety of benefits and may be particularly useful for certain imaging contexts, such as acquiring images of soft tissues in the human body. However, the various components and sub-systems of a typical MRI system, such as the gradient drivers, the RF transmit chain, the RF receiver, and the patient handling system may impose considerable, but transitory, power requirements on the system. For example, while the system power requirements are minimal when no scan is being performed, during certain scan protocols the momentary power requirement becomes extremely high, resulting in high currents drawn from the AC mains which typically power the system. Thus, in practice MRI systems may have a high peak-power to average-power ratio. The peak power requirement drives the size of the electrical installation and, hence, the provided electrical installation is typically oversized relative to average load. This scenario may become more pronounced in future as the gradient power requirements are likely to increase significantly with wide bore MRI systems used for neurological scans, which may lead to the peak power requirement during scanning increasing by multiple folds.

BRIEF DESCRIPTION

In one embodiment, a magnetic resonance imaging (MRI) system power architecture is provided. In accordance with this embodiment, the power architecture comprises: an AC mains input; a rectifier having an AC link input and a DC link output; a plurality of loads connected to the DC link output, wherein the loads comprise at least a radiofrequency amplifier power supply and a gradient amplifier power supply; and one or more energy storage elements connected to the DC link output between the rectifier and the plurality of loads.

In a further embodiment, a magnetic resonance imaging (MRI) system power architecture is provided. In accordance with this embodiment, the power architecture comprises: a main distribution panel (MDP) configured to receive three-phase AC power and having an AC link output; a rectifier configured to receive the AC link and to output a DC link; a plurality of loads connected to the DC link; one or more energy storage elements connected to the AC link output between the MDP and the rectifier; and a DC/AC isolated or non-isolated converter positioned between the one or more energy storage elements and the AC link output.

In an additional embodiment, a method for providing power to components of a magnetic resonance imaging system is provided. In accordance with this method, a main distribution panel (MDP) configured to receive three-phase AC power as an input is provided. A plurality of loads comprising at least a radiofrequency amplifier and a gradient amplifier is also provided. The plurality of loads are configured to receive DC power. A rectifier positioned between the MDP and the plurality of loads is also provided. The rectifier is configured to receive an AC power input directly or indirectly from the MDP and to provide a DC power output directly or indirectly to the plurality of loads. In addition, one or more energy storage elements downstream of the MDP and upstream of the one or more loads are provided. The one or more energy storage elements are not incorporated into the gradient amplifier stage.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
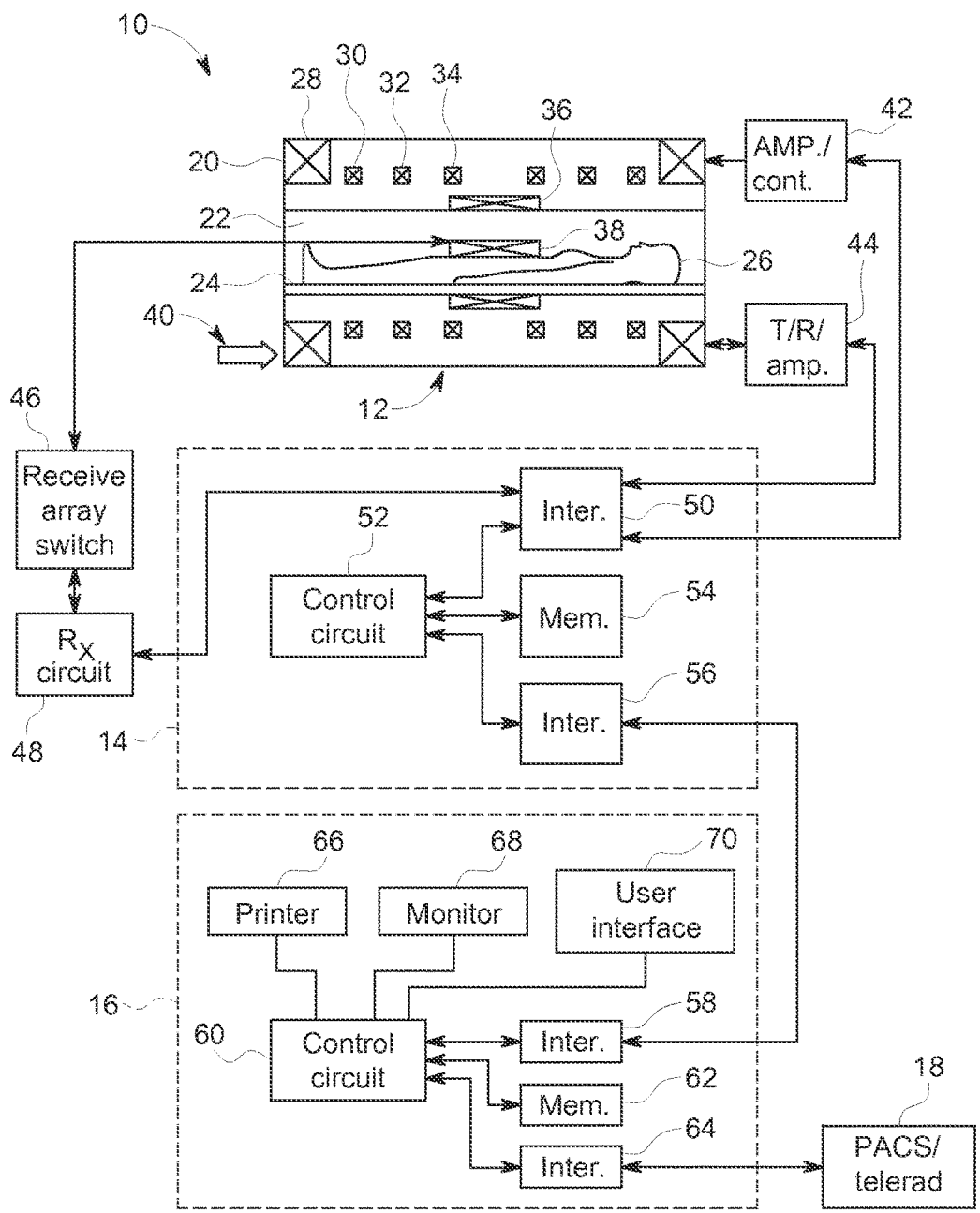
FIG. 1 is a diagrammatical illustration of an embodiment of a magnetic resonance imaging (MRI) system configured to acquire magnetic resonance images, in accordance with an aspect of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

As discussed herein, several possible implementations are disclosed for utilizing energy storage elements in conjunction with a MRI system. Similarly, various associated control mechanisms are discussed. As discussed herein, the incorporation of such energy storage elements help reduce the peak power drawn from the AC mains. Such integrated energy storage solutions may allow a hospital to use the existing electrical installation while opting for the use of high power MRI scanners, which otherwise might be unsuitable for use with the existing electrical infrastructure. Also discussed herein is the use of an integrated energy storage as energy backup to support scans when the AC mains voltage is unavailable (e.g., during an outage). In either case, the electrical installation requirement in the hospital is reduced significantly.

By way of introduction to the above-referenced concepts, the presently described approaches involve the installation of a magnetic resonance imaging (MRI) system on which imaging routines are initiated by a user (e.g., a radiologist). The MRI system may perform data acquisition, data construction, image reconstruction/synthesis, and image processing. Accordingly, referring to FIG. 1, an example of a suitable magnetic resonance imaging system 10 is illustrated schematically as including a scanner 12, a scanner control circuit 14, and system control circuitry 16. System 10 additionally includes remote access and storage systems or devices as picture archiving and communication systems (PACS) 18, or other devices such as teleradiology equipment so that data acquired by the system 10 may be accessed on- or off-site. While the MRI system 10 may include any suitable scanner or detector, in the illustrated embodiment, the system 10 includes a full body scanner 12 having a housing 20 through which a bore 22 is formed. A table 24 is moveable into the bore 22 to permit a patient 26 to be positioned therein for imaging selected anatomy within the patient 26. The selected anatomy may be imaged by a combination of patient positioning, selected excitation of certain gyromagnetic nuclei within the patient 26, and by using certain features for receiving data from the excited nuclei as they spin and process, as described below.

Scanner 12 includes a series of associated coils for producing controlled magnetic fields for exciting the gyromagnetic material within the anatomy of the subject being imaged. Specifically, a primary magnet coil 28 is provided for generating a primary magnetic field generally aligned with the bore 22. A series of gradient coils 30, 32, and 34 permit controlled magnetic gradient fields to be generated for positional encoding of certain of the gyromagnetic nuclei within the patient 26 during examination sequences. A radio frequency (RF) coil 36 is provided, and is configured to generate radio frequency pulses for exciting the certain gyromagnetic nuclei within the patient.

In addition to the coils that may be local to the scanner 12, the system 10 also includes a separate set of receiving coils 38 (e.g., a phased array of coils) configured for placement proximal (e.g., against) the patient 26. The receiving coils 38 may have any geometry, including both enclosed and single-sided geometries. As an example, the receiving coils 38 can include cervical/thoracic/lumbar (CTL) coils, head coils, single-sided spine coils, and so forth. Generally, the receiving coils 38 are placed close to or on top of the patient 26 so as to receive the weak RF signals (weak relative to the transmitted pulses generated by the scanner coils) that are generated by certain of the gyromagnetic nuclei within the patient 26 as they return to their relaxed state. The receiving coils 38 may be switched off so as not to receive or resonate with the transmit pulses generated by the scanner coils, and may be switched on so as to receive or resonate with the RF signals generated by the relaxing gyromagnetic nuclei.

The various coils of system 10 are controlled by external circuitry to generate the desired field and pulses, and to read emissions from the gyromagnetic material in a controlled manner. In the illustrated embodiment, a main power supply 40 provides power to the primary field coil 28. A driver circuit 42 is provided for pulsing the gradient field coils 30, 32, and 34, such as using the waveforms and pulse sequences as discussed herein. Such a circuit may include amplification and control circuitry for supplying current to the coils as defined by digitized pulse sequences output by the scanner control circuit 14. Another control circuit 44 is provided for regulating operation of the RF coil 36. Circuit 44 includes a switching device for alternating between the active and inactive modes of operation, wherein the RF coil 36 transmits and does not transmit signals, respectively. Circuit 44 also includes amplification circuitry for generating the RF pulses. Similarly, the receiving coils 38 are connected to switch 46 that is capable of switching the receiving coils 38 between receiving and non-receiving modes such that the receiving coils 38 resonate with the RF signals produced by relaxing gyromagnetic nuclei from within the patient 26 while in the receiving state, and they do not resonate with RF energy from the transmitting coils (i.e., coil 36) so as to prevent undesirable operation while in the non-receiving state. Additionally, a receiving circuit 48 is provided for receiving the data detected by the receiving coils 38, and may include one or more multiplexing and/or amplification circuits.

Scanner control circuit 14 includes an interface circuit 50 for outputting signals for driving the gradient field coils 30, 32, 34 and the RF coil 36. Additionally, interface circuit 50 receives the data representative of the magnetic resonance signals produced in examination sequences from the receiving circuitry 48 and/or the receiving coils 38. The interface circuit 50 is operatively connected to a control circuit 52. The control circuit 52 executes the commands for driving the circuit 42 and circuit 44 based on defined protocols selected via system control circuit 16. Control circuit 52 also serves to provide timing signals to the switch 46 so as to synchronize the transmission and reception of RF energy. Further, control circuit 52 receives the magnetic resonance signals and may perform subsequent processing before transmitting the data to system control circuit 16. Scanner control circuit 14 also includes one or more memory circuits 54, which store configuration parameters, pulse sequence descriptions, examination results, and so forth, during operation. The memory circuits 54, in certain embodiments, may store instructions for implementing at least a portion of the energy storage control techniques described herein.

Interface circuit 56 is coupled to the control circuit 52 for exchanging data between scanner control circuit 14 and system control circuit 16. Such data may include selection of specific examination sequences to be performed, configuration parameters of these sequences, and acquired data, which may be transmitted in raw or processed form from scanner control circuit 14 for subsequent processing, storage, transmission and display.

An interface circuit 58 of the system control circuit 16 receives data from the scanner control circuit 14 and transmits data and commands back to the scanner control circuit 14. The interface circuit 58 is coupled to a control circuit 60, which may include one or more processing circuits in a multi-purpose or application specific computer or workstation. Control circuit 60 is coupled to a memory circuit 62, which stores programming code for operation of the MRI system 10 and, in some configurations, the image data for later reconstruction, display and transmission. An additional interface circuit 64 may be provided for exchanging image data, configuration parameters, and so forth with external system components such as remote access and storage devices 18. Finally, the system control circuit 60 may include various peripheral devices for facilitating operator interface and for producing hard copies of the reconstructed images. In the illustrated embodiment, these peripherals include a printer 66, a monitor 68, and user interface 70 including devices such as a keyboard or a mouse.

It should be noted that subsequent to image acquisition, the system 10 may simply store the acquired data for later access locally and/or remotely, for example in a memory circuit (e.g., memory 56, 62). Thus, when accessed locally and/or remotely, the acquired data may be manipulated by one or more processors contained within an application-specific or general-purpose computer.

Figure 2:
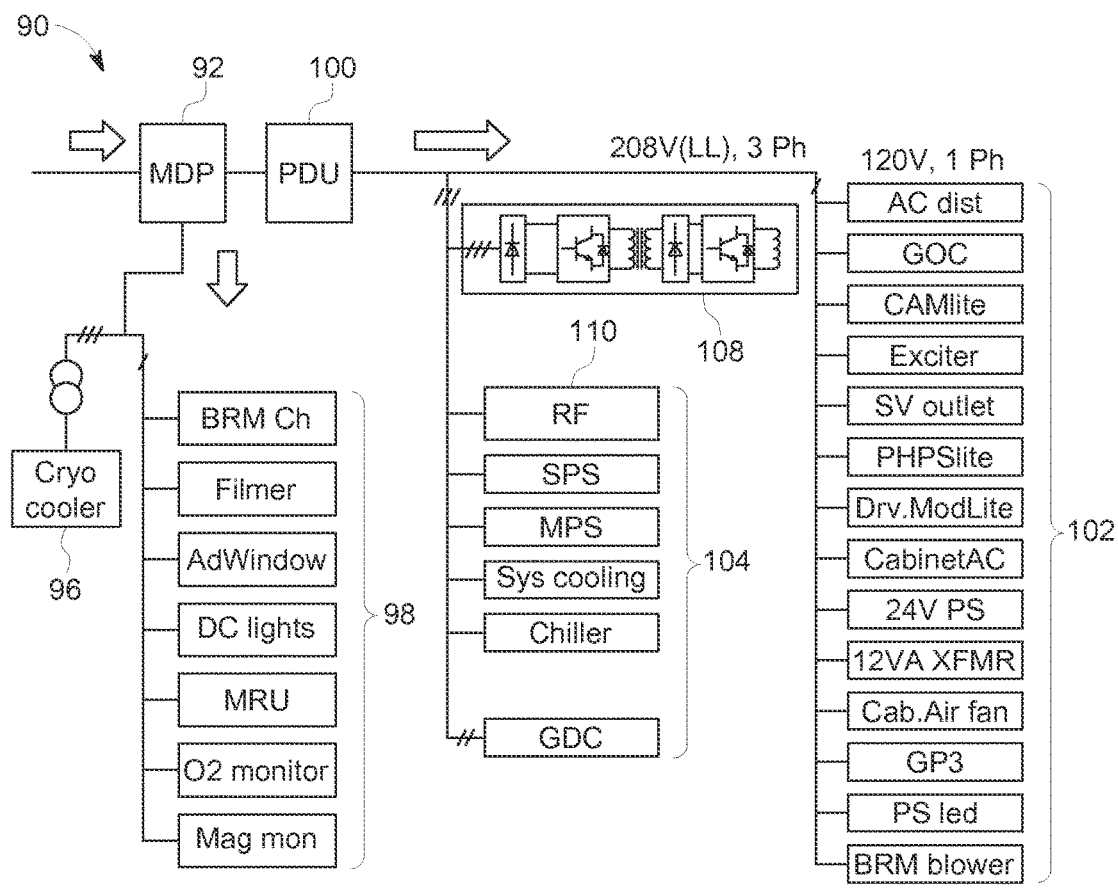
FIG. 2 depicts a system power architecture for an MRI system, in accordance with an aspect of the present disclosure.

While FIG. 1, depicts components and architecture of a generalize MRI imaging system, 10, FIG. 2 provides a more detailed description of the power architecture 90 of such a MRI system 10. In the example shown in FIG. 2, a main distribution panel (MDP) is shown which, in this example, receives three-phase power at 415 V. From this panel 92, a variety of systems may be directly powered including, but not limited to: a cryo-cooler 96, and various subsystems 98. Also connected to the depicted MDP is a power distribution unit (PDU) 100 through which other components of the MRI system 10 are powered.

In one embodiment, the PDU 100 includes a 50/60 Hz transformer. The PDU transformer supplies power to the several single-phase subsystem loads 102 and three-phase subsystem loads 104. As many of these loads can be re-configured to receive a DC input, the 50/60 Hz transformer of the PDU 100 can be replaced by a High-Frequency PDU (HFPDU) which is an AC/DC converter that also meets the PDU functionalities such as providing galvanic isolation from AC mains and ground fault isolation.

With respect to those loads supplied by the PDU 100, the largest typically are the gradient amplifier 108 and the RF amplifier 110. The gradient amplifier 108 and RF transmit chain loads draw pulsed power from the AC mains. When a scanning operation is performed, these loads draw power in the order of several tens of kW for a few hundreds of milliseconds. Conversely, when no scan operation is occurring, the power drawn by these loads is less than a few hundred watts. That is, the draw attributable to these loads varies widely based on use.

With this in mind, the present approaches relate to the use of, and control of, an integrated energy storage in the context of a MRI imaging system. Though certain embodiments discussed herein may be described in the context of the energy storage connections on a system employing a bulk PDU 100, it should be appreciated that such examples are provided solely to facilitate explanation and other PDU contexts are also encompassed by the present approaches. For example, the implementations discussed herein can also be extended to MRI imaging systems employing HFPDU as well.

With the preceding discussion in mind, an MRI imaging system 10 configured with an integral energy storage, as discussed herein, may offer various benefits. For example, the energy storage integrated with the MRI imaging system 10 may serve either or both of the following purpose: (1) peak power shaving (in which the peak power drawn from the AC mains is limited or reduced by using the energy storage) and/or (2) energy back up (when there is an outage in the AC mains, the energy storage supports scans without interruption). Furthermore, in another embodiment, when used for peak power shaving, the energy storage can be preferentially (or only) associated with those loads that have a high peak-to-average power ratio (e.g., the gradient amplifiers chain and/or the RF amplifier chain).

Figure 3:
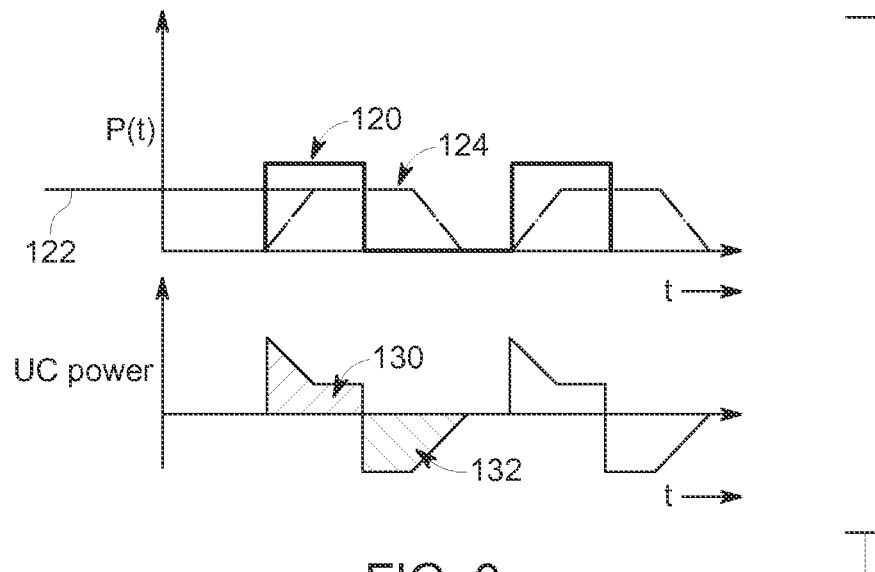
FIG. 3 graphically illustrates a peak power shaving application using energy storage elements, in accordance with an aspect of the present disclosure.

In addition, embodiments allowing peak power shaving may enable a hospital to use an existing electrical installation (e.g. cabling, distribution transformer, uninterrupted power supply (UPS), breaker etc.) while installing MRI scanners that have higher peak power requirements. This may also reduce the effect of source impedance and prevent the load voltage from dipping severely during peak power demands. By way of example, FIG. 3 graphically demonstrates one example, where an energy storage (here an ultracapacitor (UC)) is used in a peak power shaving application. Here, power as a function of time (P(t)) is shown in the top graph and energy storage power (e.g., UC power) is shown in the bottom graph, with time (t) being shown along the x-axis of both graphs. In this example, when the load power 120 is more than what the AC mains can supply (mains power 124 and main power limit 122) at a given time, the UC (bottom graph) supplies the power (UC discharge 130) to meet the load demand 120. When the load demand 120 is low, the UC charges (UC charge 132) back from the AC mains. When used in such a peak shaving application, the energy storage solution may be any suitable storage medium including, but not limited to, an ultracapacitor, a bulk capacitor bank, a battery (e.g. lithium ion battery) or a combination of battery and capacitors.

In systems in which the energy storage is employed for backup power, it may be possible to not employ a separate, external uninterrupted power supply (UPS). Instead, the energy storage (such as a battery bank of lead acid batteries, lithium ion, batteries, batteries with bulk capacitors, and so forth) is used to power the imaging system in the event that the main AC power goes down.

With the preceding in mind, an energy storage component (e.g., an ultracapacitor, a bulk capacitor bank, a battery or battery bank (e.g. lead acid or lithium ion batteries) or a combination of battery and capacitors) may be integrated into a MRI imaging system in a variety of configurations, certain examples of which are listed below.

Figure 4:
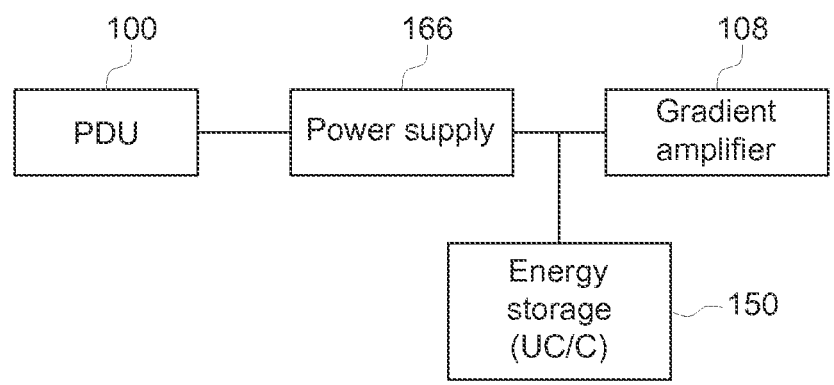
FIG. 4 depicts a prior art implementation in which energy storage is incorporated at the gradient driver stage.

To appreciate distinctions that may be drawn, it may be noted that, in other energy storage integration approaches, the energy storage component may be integrated at the gradient driver stage, as shown in FIG. 4. In particular, in the approach shown in FIG. 4, integration of the energy storage 150 is between the gradient amplifier power supply 166 and the gradient amplifier 108. This configuration might employ one energy storage 150 for each gradient axis (i.e., x, y, and z axes) or a single energy storage 150 with three (i.e., x, y, and z) DC/DC converters providing galvanic isolation to connect the energy storage 150 to the input of the gradient amplifier 108, thus incorporating greater flexibility while yielding limited gains in power flexibility.

This is in contrast to the present approaches, as shown below, in which the respective energy storage components are provided upstream of the respective component power supplies, such as gradient amplifier power supply 166. With respect to the integrated energy storage implementations discussed herein, it may be appreciated that several energy storage elements (or types of energy storage elements) may be employed in a given embodiment, though for simplicity such a configuration may be represented and discussed herein as a single or aggregate energy storage. When using several types of energy storage elements, the energy storage elements can all be connected in parallel across the DC link. In such implementations, individual charge/discharge control of the energy storage elements may not be possible. Alternatively, the energy storage elements can be integrated through converters to the DC link. In another embodiment, one of the energy storage elements can be directly connected to the DC link while another is connected to the DC link through a converter.

Turning to FIGS. 5-14 and the corresponding discussion, these figures and passages describe at a high-level a variety of embodiments representative of certain of the present approaches. As will be appreciated, these examples are not exhaustive, and other embodiments consistent with the presently described approaches are covered by the present discussion. Further, the present examples and figures are described so as to simplify explanation. As a result, certain components and functionality may be described separately to facilitate explanation. However, it should be understood that, in real-world implementations, such separate components, circuitry, and/or functionality may be integrated into single components or circuits so as to simplify fabrication and system complexity. For example, in certain described embodiments, a rectifier 162 has been represented as a separate block outside of a HFPDU 160. However, in a manufactured system, the rectifier 162 can be an integral part of a HFPDU 160. Similarly other components or parts shown as discrete blocks for the purpose of explanation should be understood to be capable of combination in practice.

Figure 5:
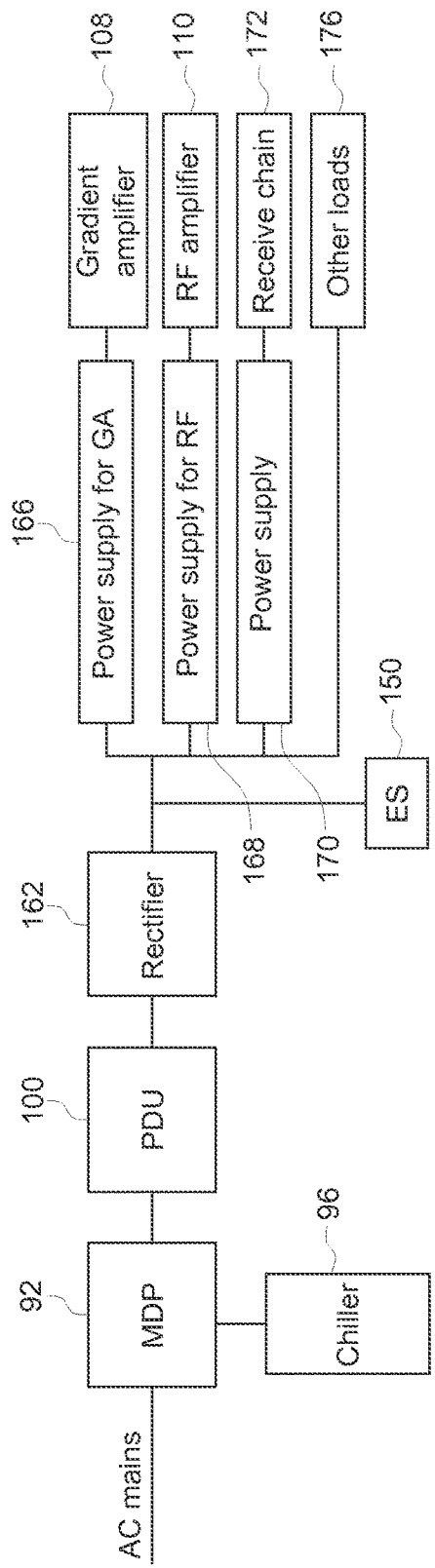
FIG. 5 depicts a first embodiment integrating an energy storage with an MRI system, in accordance with an aspect of the present disclosure.
Figure 6:
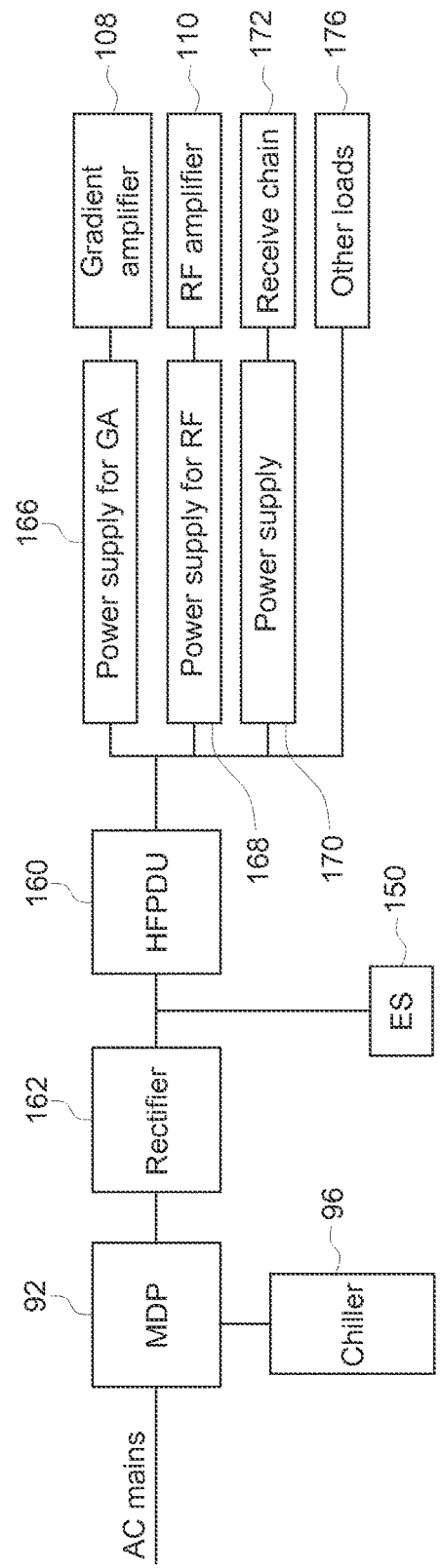
FIG. 6 depicts a second embodiment integrating an energy storage with an MRI system, in accordance with an aspect of the present disclosure.

With the preceding in mind, a variety of illustrative examples are provided to further illustrate the present approaches. For example, turning to FIGS. 5 and 6, in these implementations the energy storage 150 is connected directly to the DC link created by a passive input rectifier 162 (i.e., a passive front-end stage). The implementations shown in FIGS. 5 and 6 may be useful in contexts where the AC mains impedance is high. FIG. 5 depicts an implementation employing a bulk PDU 100 while FIG. 6 depicts the use of a HFPDU 160. In these examples, the energy storage 150 connects (in FIG. 5) between the rectifier 162 and the downstream gradient amplifier power supply 166, RF amplifier power supply 168, the power supply 170 for the receive chain 172, and other downstream loads 176. In FIG. 6 the energy storage 150 connects between the rectifier 162 and HFPDU 160, which in turn interfaces with the remaining downstream components.

With respect to the control of the energy storage element(s) 150 in the configurations shown in FIGS. 5 and 6, when there is a peak load power demand, the energy storage 150 discharges and supports the load power. The AC mains current is indirectly limited due to high source impedance in situations where the AC mains impedance is high. After the peak discharge, the energy storage 150 is charged by the AC mains. It may be noted that the charging and discharging currents are typically not controlled in such a case.

Figure 7:
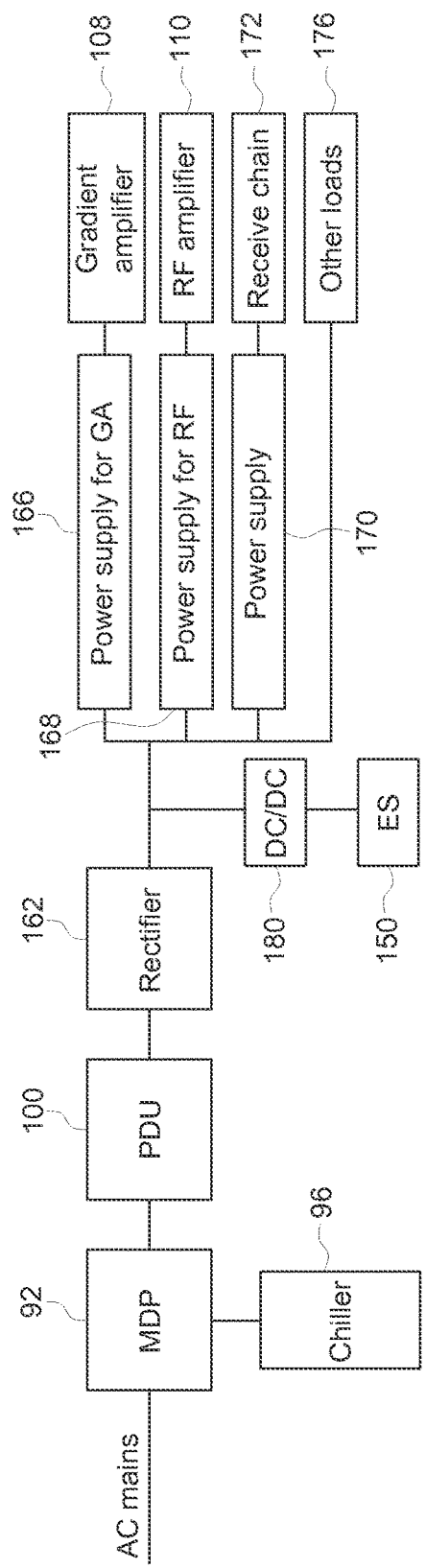
FIG. 7 depicts a third embodiment integrating an energy storage with an MRI system, in accordance with an aspect of the present disclosure.
Figure 8:
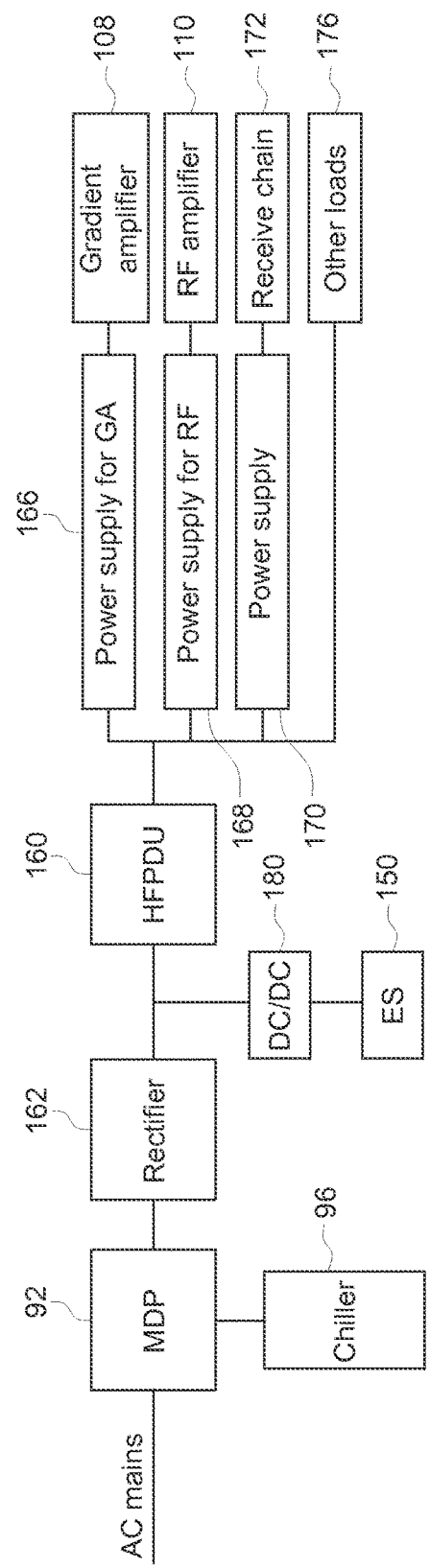
FIG. 8 depicts a fourth embodiment integrating an energy storage with an MRI system, in accordance with an aspect of the present disclosure.

Turning to FIGS. 7 and 8, implementations are depicted in which the energy storage 150 is connected through a DC/DC converter 180 (which may or may not provide galvanic isolation) to the DC link created by the passive rectifier 162 (i.e., a passive front-end stage). FIG. 7 depicts an implementation employing a bulk PDU 100 while FIG. 8 depicts the use of a HFPDU 160. In these examples, the energy storage 150 connects (in FIG. 7) through the DC/DC converter 180 downstream of the rectifier 162 and upstream from the gradient amplifier power supply 166, RF amplifier power supply 168, the power supply 170 for the receive chain 172, and other downstream loads 176. In FIG. 8 the energy storage 150 connects through the DC/DC converter 180 downstream of the rectifier 162 and upstream from the HFPDU 160, which in turn interfaces with the remaining downstream components.

With respect to the control of the energy storage element(s) 150 in the configurations shown in FIGS. 7 and 8, when there is a peak load power demand, the energy storage DC/DC converter 180 may be controlled to discharge energy from the energy storage 150 in order to achieve one or both of the following: (1) indirectly limit the AC mains current below a certain value, and/or (2) reduce the effect of source (AC mains) impedance and prevent the DC link voltage from dipping below a certain threshold. After the peak discharge, the energy storage 150 may be charged from the AC mains through the DC/DC converter 180.

It may be noted that, with respect to the preceding examples, certain conventional MRI imaging systems employ a passive front-end diode rectifier (e.g., passive rectifier 162). Hence, the energy storage 150 connection options described with respect to FIGS. 5-8 maybe suitable for retrofitting an existing MRI system using a passive rectifier 162 to include one or more energy storage elements 150. In such a retrofit context, the added energy storage capabilities may be used, as discussed herein, to reduce the peak power drawn from the AC mains and/or to extend the system capability to support high power scans, thus allowing a newer or higher power system to be supported by existing electrical infrastructure. While the above examples have been noted particularly as being suitable for a retrofit type implementation, it should be appreciated that other examples and implementations discussed herein may be suitable for use in a retrofit implementation, i.e., modifying an existing architecture by adding energy storage and/or converter components, as well as control circuitry, to an existing power architecture to enhance the capabilities provided by that power architecture.

Figure 9:
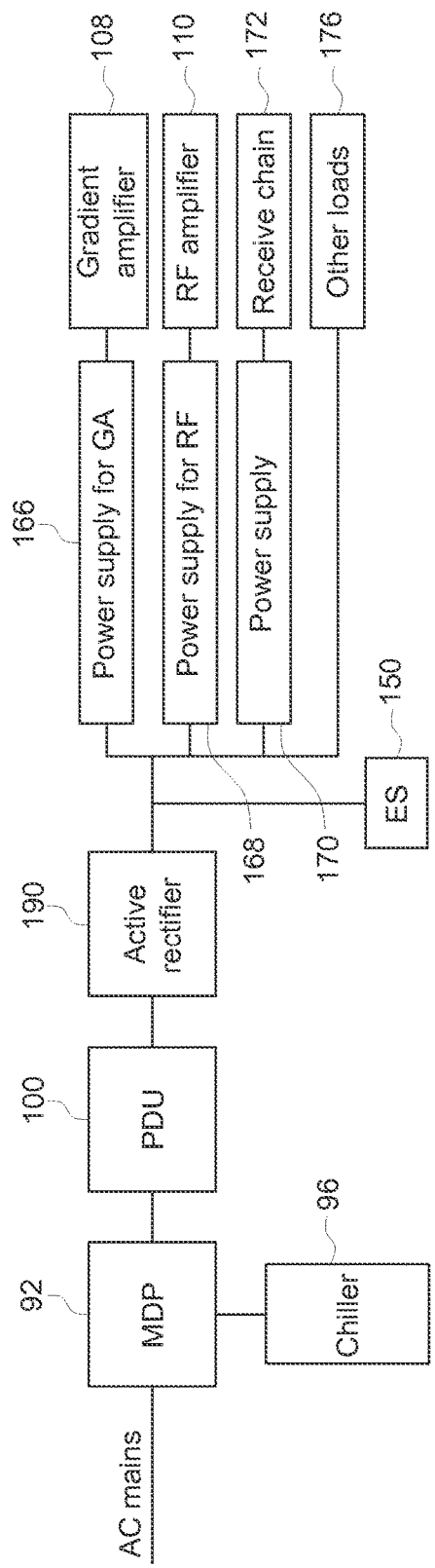
FIG. 9 depicts a fifth embodiment integrating an energy storage with an MRI system, in accordance with an aspect of the present disclosure.
Figure 10:
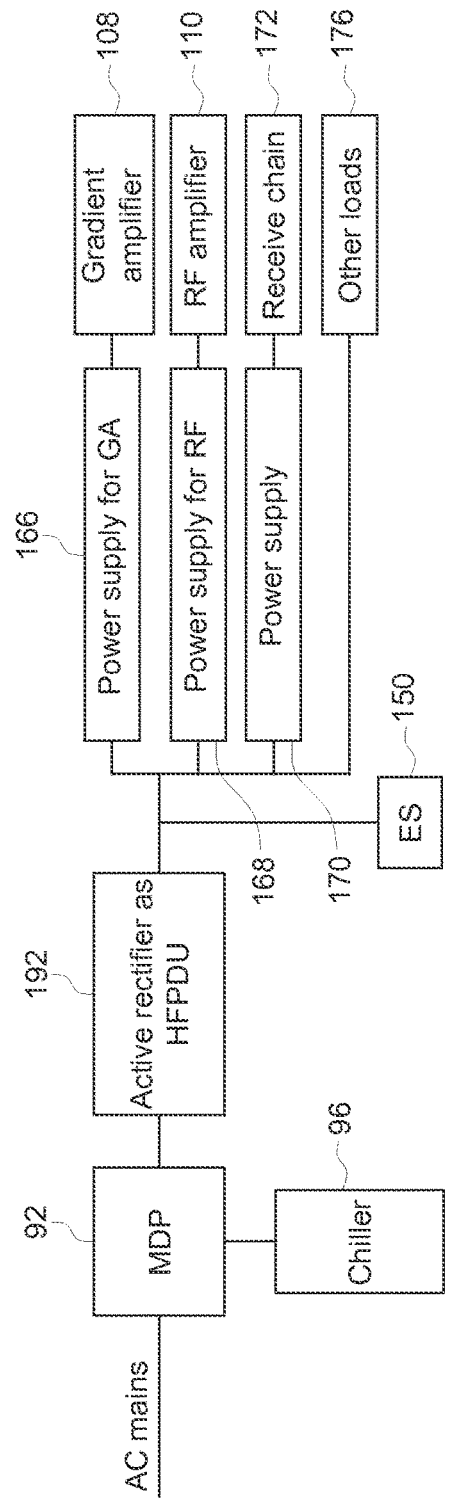
FIG. 10 depicts a sixth embodiment integrating an energy storage with an MRI system, in accordance with an aspect of the present disclosure.

Turning to FIGS. 9 and 10, a variation on the preceding approaches is shown in which an active front end (e.g., an active AC/DC converter) is provided. In particular, the active front end may take the form of a three-phase active rectifier (shown) or a passive rectifier followed, by a DC/DC (isolated or non-isolated) converter, and so forth. FIG. 9 depicts an implementation employing a bulk PDU 100 while FIG. 10 depicts the use of an active rectifier 192 functioning as both rectifier and as a HFPDU. In both of these examples, the energy storage 150 connects downstream of the active rectifier 190, 192 (i.e., to the DC link) and upstream from the gradient amplifier power supply 166, RF amplifier power supply 168, the power supply 170 for the receive chain 172, and other downstream loads 176.

With respect to the control of the energy storage element(s) 150 in the configurations shown in FIGS. 9 and 10, when there is a peak load power demand, the active front end converter (i.e., rectifier 190, 192) may be controlled to directly limit the current from the AC mains. The energy storage 150 discharges to support the load power demand. After the peak discharge, the energy storage 150 may be charged from the AC mains through the active front end converter 190, 192. The energy storage 150 charging and discharging currents are controlled in such a scenario.

Figure 11:
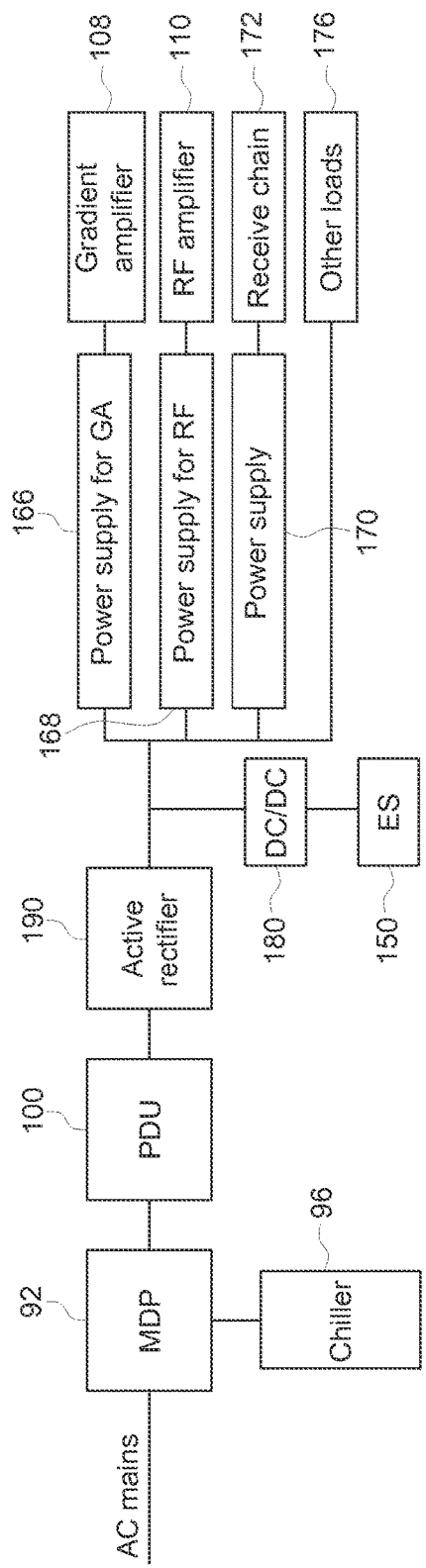
FIG. 11 depicts a seventh embodiment integrating an energy storage with an MRI system, in accordance with an aspect of the present disclosure.
Figure 12:
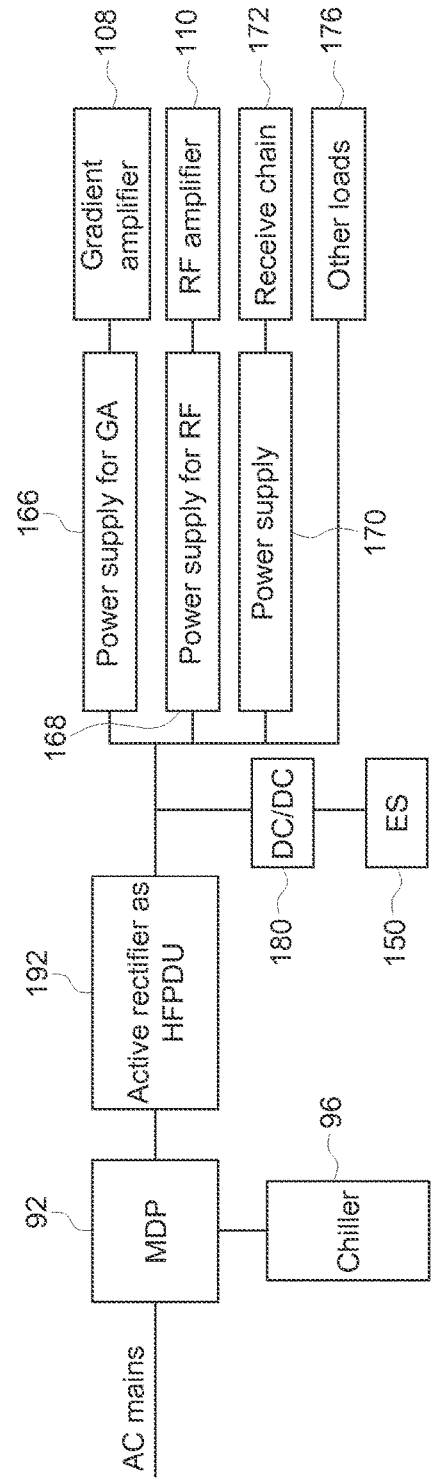
FIG. 12 depicts a eighth embodiment integrating an energy storage with an MRI system, in accordance with an aspect of the present disclosure.

In a further active front-end variation, shown in FIGS. 11 and 12, the energy storage 150 is connected through a DC/DC converter 180 (which may or may not provide galvanic isolation) to the DC link created by an active AC/DC converter (i.e., active rectifier 190, 192). FIG. 11 depicts an implementation employing a bulk PDU 100 while FIG. 12 depicts the use of an active rectifier 192 functioning as both rectifier and as a HFPDU. In both of these examples, the energy storage 150 connects, through the DC/DC converter 180, downstream of the active rectifier 190, 192 (i.e., to the DC link) and upstream from the gradient amplifier power supply 166, RF amplifier power supply 168, the power supply 170 for the receive chain 172, and other downstream loads 176.

With respect to the control of the energy storage element(s) 150 in the configurations shown in FIGS. 11 and 12, the power from both the AC mains as well as the energy storage are actively controlled. As discussed in the case of previous examples, energy storage is controllably discharged to meet the peak power demand and is charged from ac mains when the load demand is low.

Figure 13:
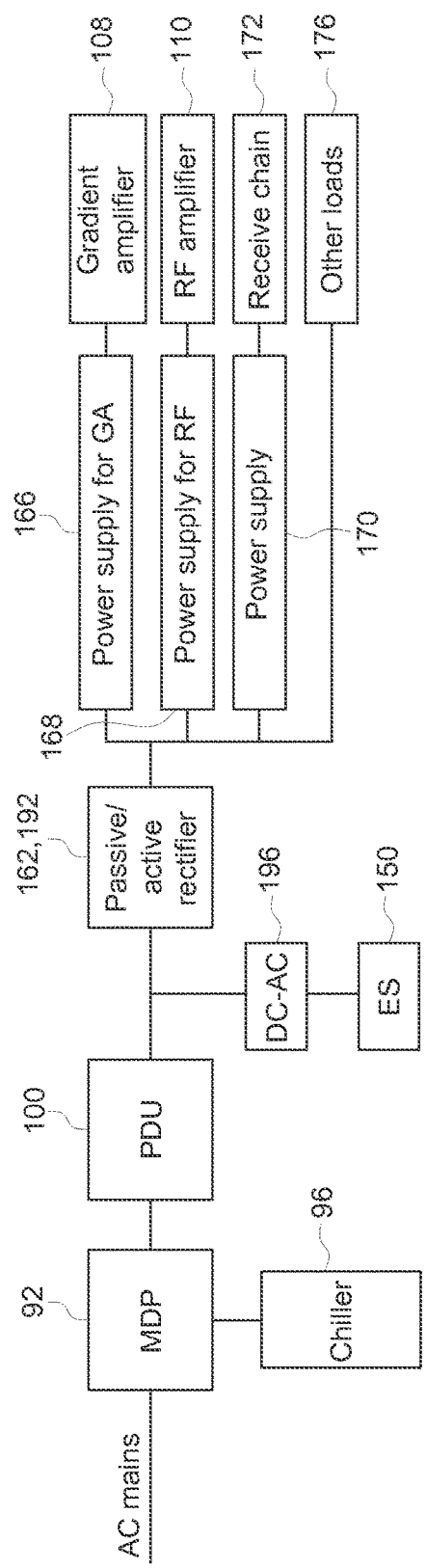
FIG. 13 depicts a ninth embodiment integrating an energy storage with an MRI system, in accordance with an aspect of the present disclosure.
Figure 14:
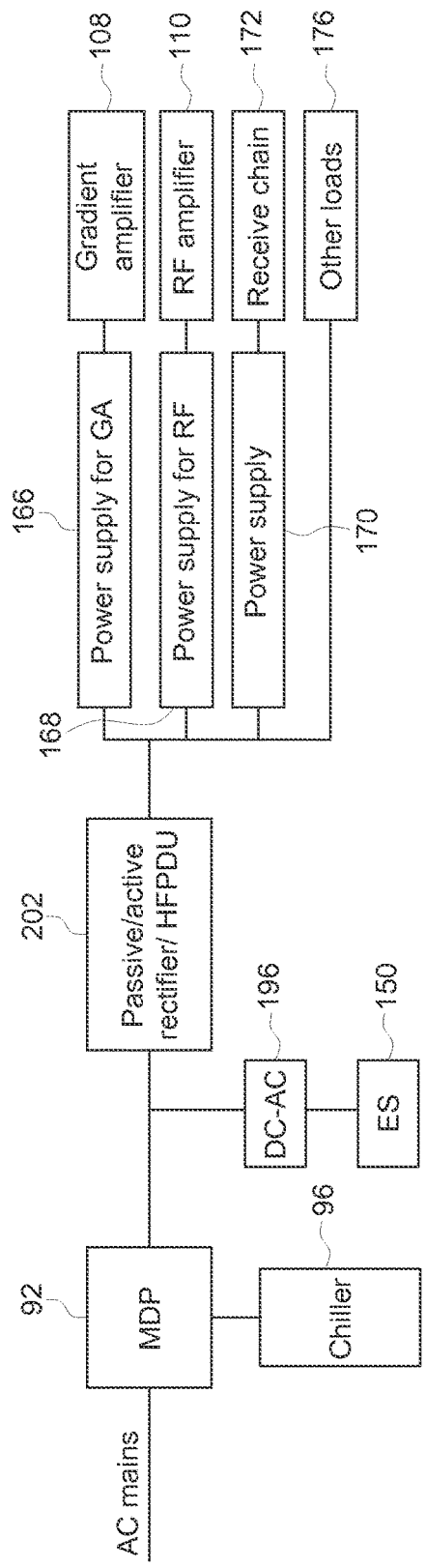
FIG. 14 depicts a tenth embodiment integrating an energy storage with an MRI system, in accordance with an aspect of the present disclosure.

In a further implementation, shown in FIGS. 13 and 14, the energy storage 150 may be connected to the AC mains link through a DC/AC converter 196 (which may or may not provide galvanic isolation). FIG. 13 depicts an implementation employing a bulk PDU 100 and either a passive rectifier 162 or active rectifier 192 while FIG. 14 depicts the use of either a passive or active rectifier functioning as both rectifier and as a HFPDU 202. In these examples, the energy storage 150 connects (in FIG. 13) through the DC/AC converter 196 downstream of the PDU 100 and upstream of the rectifier 162, 192. In FIG. 14 the energy storage 150 connects through the DC/AC converter 196 downstream of the MDP 92 and upstream from the rectifier/HFPDU 202, which in turn interfaces with the remaining downstream components.

With respect to the control of the energy storage element(s) 150 in the configurations shown in FIGS. 13 and 14, one embodiment of controlling the energy storage voltage is described. In this embodiment, the approach may be similar to a context in which a line-interactive UPS is connected to the AC mains. However, unlike the case of a line interactive UPS, which supports the load only when the AC mains undergoes an outage, the energy storage 150 and energy storage converter 196 in these examples, irrespective of the state of the AC mains, always meets the load demand.

With the preceding examples of energy storage 150 configurations, a more detailed explanation using an example configuration is provided. In this example, the energy storage 150 and converter 180 configurations shown in FIGS. 7 and 8 is simulated, with energy storage 150 being integrated with a gradient load 108. The following discussion presents the simulation models and results.

Figure 15:
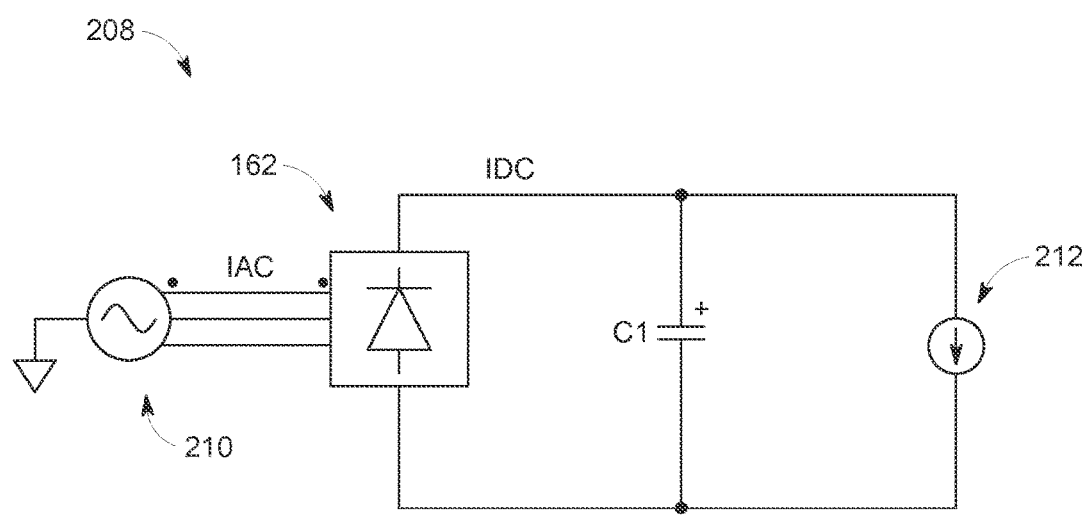
FIG. 15 depicts a baseline circuit for handling MRI power with no energy storage.
Figure 16:
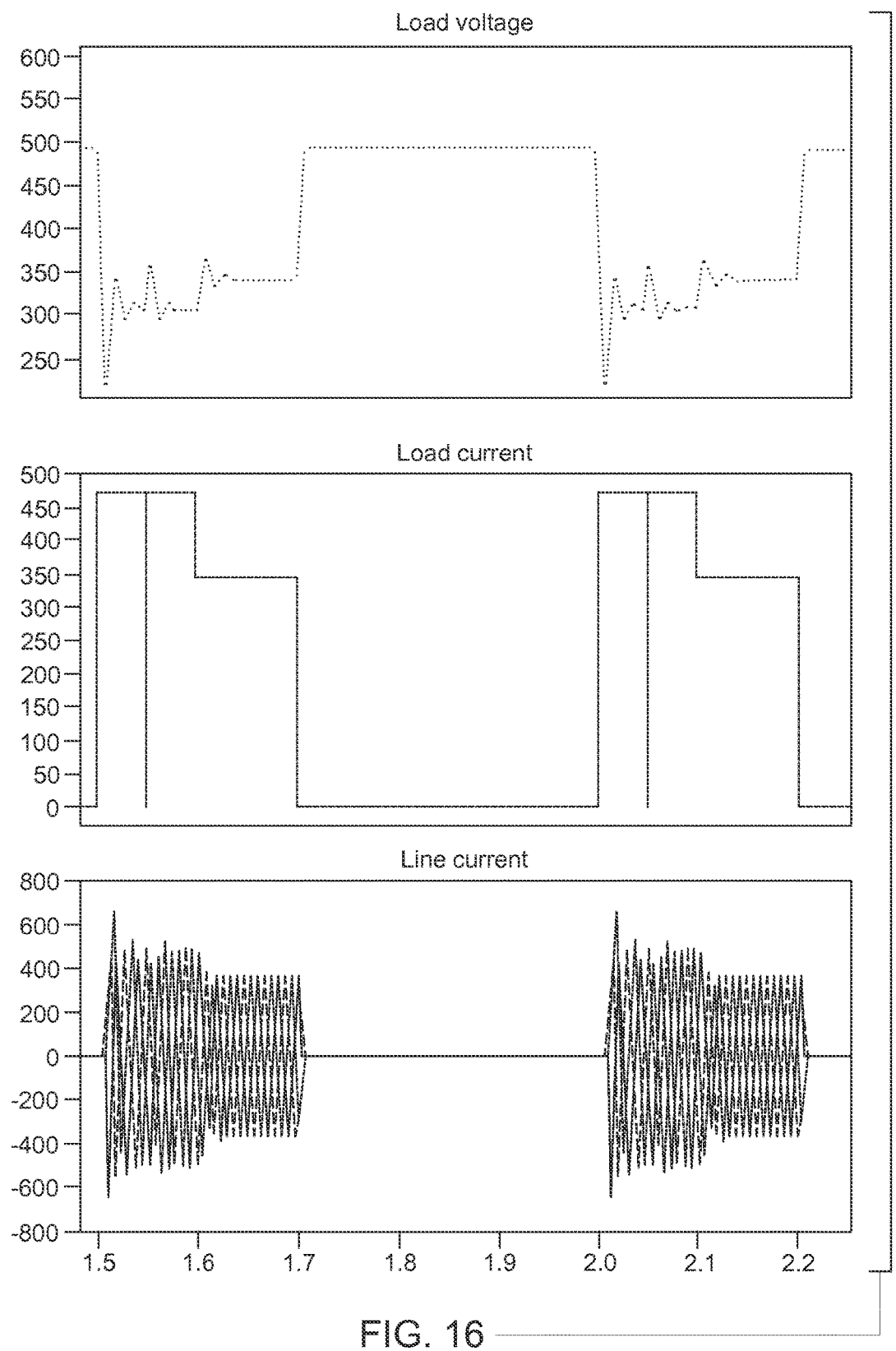
FIG. 16 graphically depicts various power profile aspects of the circuit of FIG. 15 in the presence of a pulsating load.

With this in mind, FIG. 15 shows a baseline case (circuit 208) in which a pulsating load 212, such as an MRI scanner 10 is connected to three-phase AC mains 210 through a diode bridge (passive) rectifier 162. There is no energy storage integrated in this baseline case. For the sake of simplicity, it is assumed that the entire pulsating load 212 appears directly at the input mains 210. In the accompanying graphs, the operation of circuit 208 is shown in terms of load voltage (FIG. 16, top graph), load current (FIG. 16, middle graph), and line current (FIG. 16, bottom graph). It may be noticed that the presence of the diode rectifier 162 results in an unregulated DC link voltage. Also the current drawn from the AC mains 210 exceeds 400 A for the given peak power drawn by the gradient driver (i.e., load 212). This high current, therefore, implies the need for a bigger electrical installation.

Figure 17:
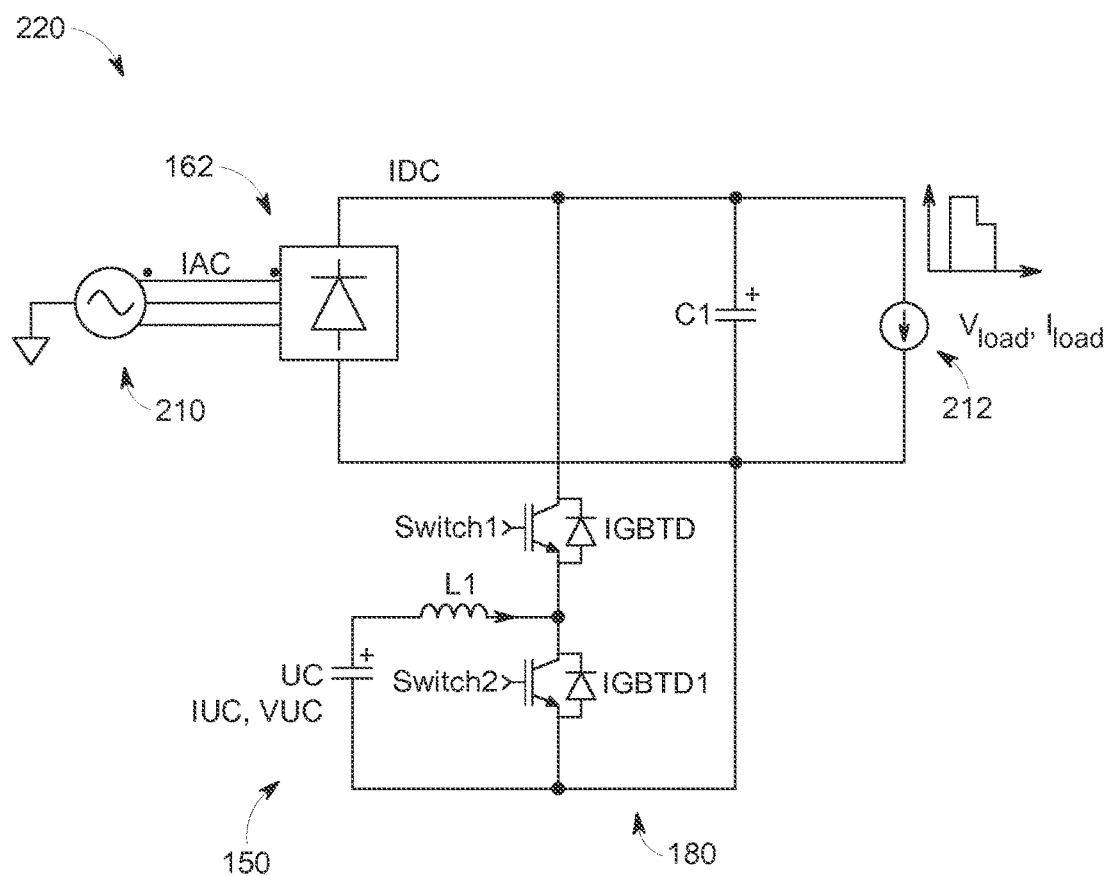
FIG. 17 depicts a circuit incorporating an energy storage element, in accordance with an aspect of the present disclosure.

Conversely, FIG. 17 shows (circuit view 220) the system of FIG. 15 with an energy storage 150 integrated through a bidirectional DC/DC converter 180 to the DC link (as generally discussed with respect to FIG. 7, for example). An electric double layer capacitor (EDLC, also known as ultracapacitor (UC)) is shown as the energy storage element 150 in this example though other types of suitable energy storage elements 150 may be used (in other implementations) in place of or in addition to such an ultracapacitor. As shown graphically in the preceding FIG. 3, power is shared between AC mains 210 and EDLC (e.g., energy storage 150) during a pulsing period and power drawn during a non-pulsing period is utilized by the EDLC to charge back (e.g., energy storage 150). This release of energy from EDLC during peak load power duration, results in reducing the power and hence the current drawn from the AC mains 210.

Figure 18:
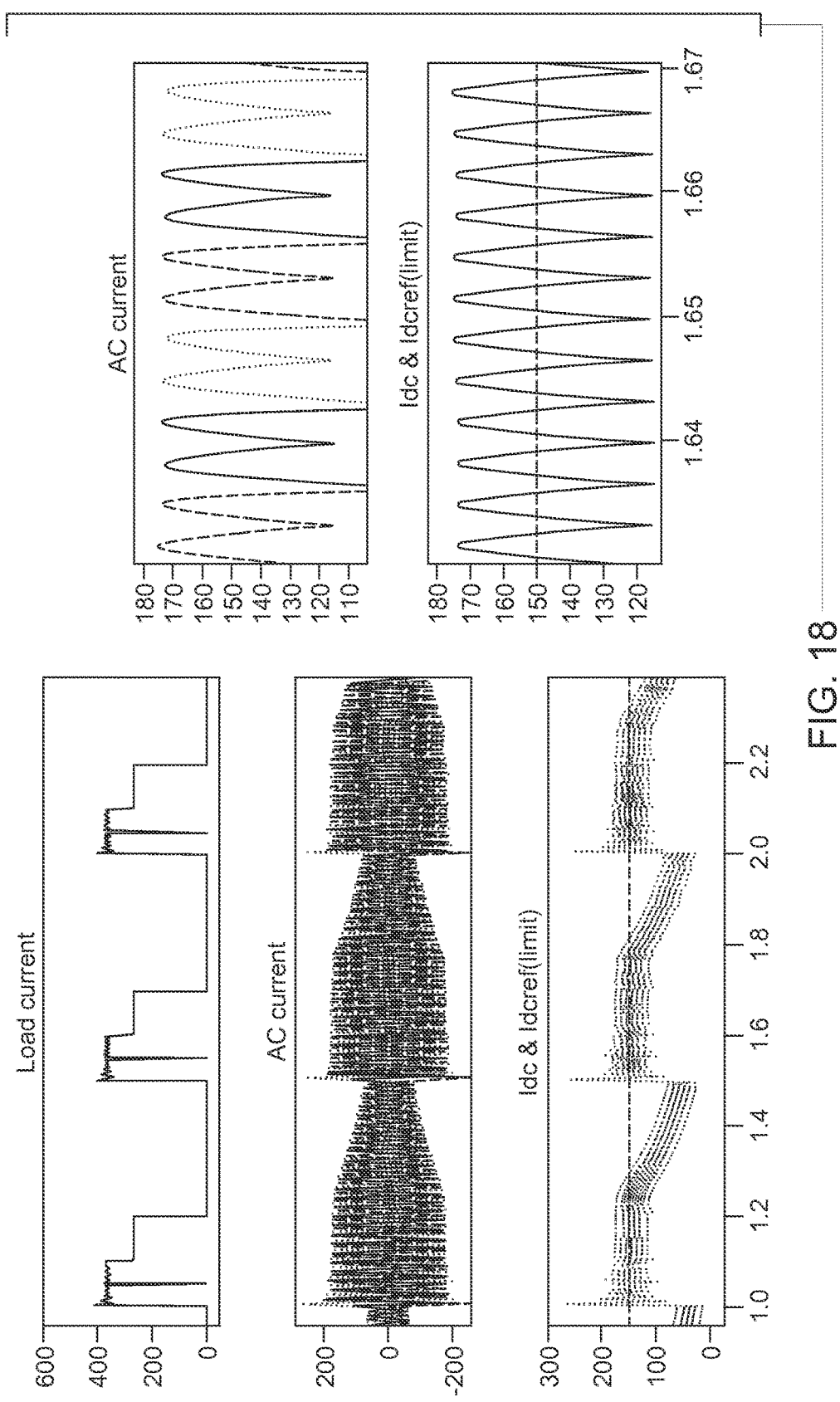
FIG. 18 graphically depicts various power profile aspects of the circuit of FIG. 17, in accordance with an aspect of the present disclosure.

Using an appropriate control scheme, the energy storage converter 180 is controlled to discharge during peak load demand and charge when the load demand is low. In this example, for the same power profile discussed in FIG. 16, FIG. 18 graphically demonstrates a reduction in the AC-side mains current (FIG. 16, bottom graph, FIG. 18, middle, left graph) when employing an energy storage 150. It may be noticed that in this example, by appropriately setting the control parameters, the AC mains current is limited to 150. It may also be noticed that with the loading on the AC mains being reduced, the DC link voltage dips and oscillations when peak power is drawn from mains (see FIG. 3) is also reduced significantly.

Technical effects of the invention include integration of an energy storage in an MRI system, allowing hospitals to install high power MRI systems with an existing electrical installation. Further technical effects include the ability to retrofit existing MRI power architectures to add a 'drop in' energy storage and control circuitry to an existing system. Such a retrofit may reduce the peak power and hence the tariff on peak power. Other technical effects include eliminating the need for an uninterrupted power supply for an MRI system, such as when a battery bank is also integrated with the MRI system.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A magnetic resonance imaging (MRI) system power architecture, comprising:
   an AC mains;
   a main distribution panel (MDP) connected to the AC mains;
   a rectifier having an AC link input and a DC link output;
   a power distribution unit (PDU) positioned between the MDP and rectifier;
   a plurality of loads connected to the DC link output, wherein the plurality of loads comprises at least a radiofrequency amplifier power supply and a gradient amplifier power supply; and
   one or more energy storage elements disposed between the rectifier and the plurality of loads and connected to the DC link output.

2. The magnetic resonance imaging system power architecture of claim 1, wherein the rectifier is a passive rectifier.

3. The magnetic resonance imaging system power architecture of claim 1, further comprising:
   a DC/DC isolated or non-isolated converter positioned between the one or more energy storage elements and the DC link output.

4. The magnetic resonance imaging system power architecture of claim 1, further comprising:
   a passive front-end HFPDU positioned before the plurality of loads.

5. The magnetic resonance imaging system power architecture of claim 1, wherein the rectifier is an active rectifier.

6. The magnetic resonance imaging system power architecture of claim 1, wherein the one or more energy storage elements comprise one or more of an ultracapacitor, a bulk capacitor bank, a battery or battery bank, or a combination of battery and capacitors.

7. The magnetic resonance imaging system power architecture of claim 1, wherein the plurality of loads further comprises a power supply for an RF transmit chain.

8. The magnetic resonance imaging system power architecture of claim 1, further comprising:
   control circuitry for controlling discharge and recharge of the one or more energy storage elements, wherein the control circuitry directs power from the one or more energy storage elements during application of a pulse sequence by the magnetic resonance imaging system and charges the one or more energy storage elements during a non-pulsing period or if a peak demand by the pulse sequence is less than an allowable peak power from the AC link input.

9. The magnetic resonance imaging system power architecture of claim 1, further comprising:
   control circuitry for controlling discharge and recharge of the one or more energy storage elements, wherein the control circuitry directs power from the one or more energy storage elements in an event of an outage of the AC mains.

10. A magnetic resonance imaging (MRI) system power architecture, comprising:
    a main distribution panel (MDP) configured to receive three-phase AC power and having an AC link output;
    a rectifier configured to receive the AC link output and coupled to a DC link;
    a plurality of loads connected to the DC link;
    one or more energy storage elements connected to the AC link output between the MDP and the rectifier; and
    a DC/AC isolated or non-isolated converter positioned between the one or more energy storage elements and the AC link output.

11. The magnetic resonance imaging system power architecture of claim 10, wherein the plurality of loads comprises one or more of a radiofrequency amplifier power supply, a gradient amplifier power supply, or a power supply for an RF transmit chain.

12. The magnetic resonance imaging system power architecture of claim 10, further comprising:
    a power distribution unit (PDU) positioned between the MDP and rectifier.

13. The magnetic resonance imaging system power architecture of claim 10, wherein the rectifier is a passive rectifier.

14. The magnetic resonance imaging system power architecture of claim 10, wherein the rectifier is an active rectifier.

15. The magnetic resonance imaging system power architecture of claim 10, further comprising:
    a high-frequency power distribution unit (HFPDU) positioned between the MDP and the plurality of loads.

16. The magnetic resonance imaging system power architecture of claim 10, wherein the one or more energy storage elements comprise one or more of an ultracapacitor, a bulk capacitor bank, a battery or battery bank, or a combination of battery and capacitors.

17. A method for providing power to components of a magnetic resonance imaging system, the method comprising:
- providing a main distribution panel (MDP) configured to receive three-phase AC power as an input;
- providing a plurality of loads comprising at least a radiofrequency amplifier and a gradient amplifier, wherein the plurality of loads is configured to receive DC power;
- providing a rectifier positioned between the MDP and the plurality of loads, wherein the rectifier is configured to receive an AC power input directly or indirectly from the MDP and to provide a DC power output directly or indirectly to the plurality of loads; and
- providing one or more energy storage elements downstream of the MDP and upstream of the one or more of the plurality of loads, wherein the one or more energy storage elements are not incorporated into the gradient amplifier.

18. The method of claim 17, wherein the one or more energy storage elements is configured to provide DC power downstream of the rectifier and upstream of the one or more of the plurality of loads.

19. The method of claim 17, wherein the one or more energy storage elements is configured to provide DC power to a DC/AC converter that provides AC power downstream of the MDP and upstream of the rectifier.

* * * * *